United States Patent [19]

Powell

[11] Patent Number: 5,651,984
[45] Date of Patent: Jul. 29, 1997

[54] CONTROLLED RELEASE POTASSIUM TABLET

[75] Inventor: Thomas Clark Powell, West Alexandria, Ohio

[73] Assignee: Eurand America, Incorporated, Vandalia, Ohio

[21] Appl. No.: 404,216

[22] Filed: Mar. 14, 1995

Related U.S. Application Data

[62] Division of Ser. No. 925,717, Aug. 4, 1992, Pat. No. 5,422,122.

[51] Int. Cl.$^6$ .................................................. A61K 9/20
[52] U.S. Cl. .......................... 424/465; 424/473; 424/474; 424/458
[58] Field of Search .................... 424/465, 473, 424/458, 474

[56] References Cited

U.S. PATENT DOCUMENTS

| | | |
|---|---|---|
| 2,887,440 | 5/1959 | Greminger, Jr. et al. . |
| 3,155,590 | 11/1964 | Miller et al. ............................ 167/83 |
| 3,242,051 | 3/1966 | Hiestand et al. . |
| 3,341,416 | 9/1967 | Anderson et al. ..................... 167/83 |
| 3,354,863 | 11/1967 | Reynolds . |
| 3,476,588 | 11/1969 | Pitel . |
| 3,531,418 | 9/1970 | Fanger et al. . |
| 3,557,279 | 1/1971 | Morse . |
| 3,694,372 | 9/1972 | Anderson et al. . |
| 3,732,172 | 5/1973 | Herbig et al. . |
| 3,748,277 | 7/1973 | Wagner . |
| 3,909,444 | 9/1975 | Anderson et al. . |
| 3,939,259 | 2/1976 | Pescetti . |
| 3,957,523 | 5/1976 | Ohno et al. . |
| 3,960,757 | 6/1976 | Morishita et al. . |
| 4,138,475 | 2/1979 | McAinsh et al. . |
| 4,140,756 | 2/1979 | Gallian . |
| 4,150,110 | 4/1979 | Yoshida et al. . |
| 4,193,985 | 3/1980 | Bechgaard et al. ................... 424/19 |
| 4,259,315 | 3/1981 | Lippmann et al. .................... 424/458 |
| 4,316,884 | 2/1982 | Alam et al. . |
| 4,389,331 | 6/1983 | Samejima et al. . |
| 4,432,966 | 2/1984 | Zeitun et al. ........................ 424/21 |
| 4,462,982 | 7/1984 | Samejima et al. . |
| 4,508,702 | 4/1985 | Hsiao . |
| 4,555,399 | 11/1985 | Hsiao . |
| 4,572,833 | 2/1986 | Pedersen et al. ..................... 424/20 |
| 4,574,080 | 3/1986 | Roswall et al. ....................... 424/458 |
| 4,587,118 | 5/1986 | Hsiao . |
| 4,634,587 | 1/1987 | Hsiao ..................................... 424/19 |
| 4,713,248 | 12/1987 | Kjornaes et al. . |
| 4,716,041 | 12/1987 | Kjornaes et al. . |
| 4,748,023 | 5/1988 | Tamas et al. .......................... 424/465 |
| 4,832,955 | 5/1989 | Snipes et al. .......................... 424/456 |
| 4,863,743 | 9/1989 | Hsiao et al. ........................... 424/476 |
| 4,898,737 | 2/1990 | Panoz et al. . |
| 5,008,117 | 4/1991 | Calanchi et al. . |
| 5,032,406 | 7/1991 | Dansereau et al. ................... 424/472 |
| 5,126,145 | 6/1992 | Evenstad et al. ..................... 424/465 |
| 5,133,974 | 7/1992 | Paradissis et al. .................... 424/480 |
| 5,156,850 | 10/1992 | Wong et al. .......................... 424/473 |

FOREIGN PATENT DOCUMENTS

| | | |
|---|---|---|
| 0076515 | 4/1983 | European Pat. Off. . |
| 978265 | 12/1964 | United Kingdom . |
| 1016839 | 1/1966 | United Kingdom . |
| 1371840 | 10/1974 | United Kingdom . |

OTHER PUBLICATIONS

Samuelov, Donbrow and Friedman, *Sustained Release of Drugs from Ethylcellulos–Polyethylene Glycol Films and Kinetics of Drug Release*, "Journal of Pharmaceutical Sciences," Mar., 1979, 68:325–329.

Donbrow and Friedman, *Enhancement of permeability of ethyl cellulose films for drug penetration*, "Journal of Pharmacy and Pharmacology," Sep., 1975, 27:633–646.

Donbrow and Samuelov, *Zero order drug delivery from double–layered porous films: release rate profiles from ethyl cellulose, hydroxypropyl cellulose and polyethylene glycol mixtures*, "Journal of Pharmacy and Pharmacology," 1980, 32:463–470.

Rowe, *The effect of the molecular weight of ethyl cellulose on the drug release properties of mixed films of ethyl cellulose and hydroxypropyl methylcellulose*, "International Journal of Pharmaceutics," Mar., 1986, 29:37–41.

Donbrow and Friedman, *Permeability of films of ethyl cellulose and PEG to caffeine*, "Journal of Pharmacy and Pharmacology," Feb., 1974, 26:148–150.

Rowe, *Some Fundamental Properties of Polymeric Materials and their Application in Film Coating Formulations—A Review*, "Int. J. Pharm. Tech & Prod. Mfr.", 1982, 3:3–8.

*Primary Examiner*—Thurman K. Page
*Assistant Examiner*—William E. Benston, Jr.

[57] ABSTRACT

A pharmaceutical dosage form is prepared from a multiplicity of coated potassium chloride crystals coated with two distinct layers, the first of ethylcellulose and the second of a hydrophilic coating polymer, preferably hydroxypropylcellulose, resulting in microcapsules. These microcapsules are capable of being compressed into tablets of suitable hardness and friability with minimum quantities of excipients. The resultant controlled release tablets are useful for treatment of potassium deficiencies in humans.

10 Claims, No Drawings

CONTROLLED RELEASE POTASSIUM TABLET

This is a divisional of application Ser. No. 07/925,717 filed on Aug. 4, 1992 U.S. Pat. No. 5,422,122.

BACKGROUND OF THE INVENTION

The present invention pertains to an improved controlled release potassium chloride tablet and a process for its preparation. More particularly, the present invention relates to a potassium chloride tablet prepared from microcapsules of potassium chloride crystals coated with two distinct layers, the first of ethylcellulose and the second of a hydrophilic polymer, preferably hydroxypropylcellulose. These microcapsules are capable of being compressed into tablets of suitable hardness and friability with minimum compression and quantities of excipients.

Sustained release formulations consisting of microencapsulated pharmaceutical agents coated with a single layer composed of ethylcellulose have been disclosed. Anderson, et al. disclose aspirin coated with a single layer of ethylcellulose (U.S. Pat. No. 3,341,416). Miller, et al. disclose a process for coating aspirin crystals with a single layer of polymeric material, such as ethylcellulose (U.S. Pat. No. 3,155,590). Tamas discloses a process for the preparation of sustained release solid pharmaceutical compositions which contain crystals of an active ingredient coated with a single layer of a polymer such as ethylcellulose (U.S. Pat. No. 4,748,023). Lippman, et al. disclose a controlled release capsule containing potassium salt coated with ethylcellulose and external surfactant having an HLB in excess of 10 (U.S. Pat. No. 4,259,315).

Other standard controlled release formulations consisting of microencapsulated pharmaceutical agents coated with a single layer of a polymer mixture have been disclosed. Bechgaard, et al. disclose a controlled release tablet or capsule with contains a core comprising an active agent and coated with a diffusion membrane which is insoluble in gastrointestinal fluids which may include ethylcellulose (U.S. Pat. No. 4,193,985). Samejima, et al. disclose the coating of microcrystals with a single layer consisting of a polymer mixture, such as ethylcellulose and hydroxymethylcellulose (U.S. Pat. No. 4,462,982). Pedersen, et al. disclose a controlled release composition containing a core of active agent which may be potassium chloride coated with a water insoluble, but water diffusible, layer consisting of a mixture of a solvent, a film-forming substance which may be ethylcellulose, and a hydrophobic substance (U.S. Pat. No. 4,572,833). Roswell, et al. disclose a controlled release composition containing a core of active agent which may be potassium chloride coated with a water insoluble, but water diffusible, layer consisting of a mixture of a solvent, a film-forming substance which may be ethylcellulose, and a hydrophobic substance with particles of the active agent adhered to the coating (U.S. Pat. No. 4,574,080). Hsiao discloses a sustained release dosage form of quinidine-coated pellets coated with a single layer which consists of a mixture of ethylcellulose and hydroxypropylcellulose (U.S. Pat. No. 4,634,587). Snipes discloses controlled release potassium chloride crystals coated with a single layer of a two component polymer mixture which consists of 85–97% ethylcellulose and 3–15% of an amphiphile (U.S. Pat. No. 4,832,955). Hsiao, et al. disclose a controlled release potassium chloride tablet form for oral administration which contains potassium chloride crystals coated with a single layer which consists of a mixture of ethylcellulose and either hydroxypropylcellulose or polyethylene glycol (U.S. Pat. No. 4,863,743).

Still other sustained release formulations consisting of microencapsulated pharmaceutical agents coated with a plurality of polymeric coatings have been disclosed. Zeitoun, et al. disclose compressed tablets for disintegration in the colon which contain a core of an active ingredient and a two-layer coating, the inner coating which may be of ethylcellulose controls the diffusion of the active ingredient and an enteric outer coating of an organic polymer (U.S. Pat. No. 4,432,966). Kjornaes, et al. disclose a sustained release tablet which contains crystals of the active ingredient coated with an inner layer of an aqueous dispersion of a film-forming agent which causes adhesion between the crystals at elevated temperatures and an outer layer of a water-based, film-forming agent which prevents adhesion of the crystals during heating, imparting flowability (U.S. Pat. No. 4,716,041).

SUMMARY OF THE INVENTION

An object of the present invention is to provide a method of preparing ethycellulose microencapsulated potassium chloride crystals with a coating of a hydrophilic polymer which allows compression into tablets of suitable hardness and friability at low compaction pressures when combined with a minimum amount of excipients and having controlled dissolution characteristics.

Another object is to provide tablets comprised of the treated microencapsulated potassium chloride crystals and excipients, wherein an amount of excipients lower than that conventionally used allows manufacture of tablets containing a minimum quantity of excipients relative to the quantity of treated microencapsulated potassium chloride, thereby providing a single tablet which can deliver an effective daily dosage of potassium without being unduly large for swallowing.

A further object is to provide tablets comprised of treated microencapsulated potassium chloride and excipients which disintegrate rapidly when administered orally, thereby releasing the microencapsulated potassium chloride for rapid disintegration in the gastrointestinal tract and controlled dissolution, reducing the likelihood of localized toxicity and damage to the gastric mucosa.

A still further object is to provide a method of treating, relieving, or preventing potassium deficiency in humans with minimal adverse side effects comprising orally administering tablets comprised of an effective amount of ethylcellulose microencapsulated potassium chloride coated with a hydrophilic polymer and a minimum quantity of excipients.

Additional objects will become apparent hereinafter and still other objects will be apparent to one of ordinary skill in the art from the following disclosure.

These and other objects are accomplished according to the present invention which provides an improved controlled release potassium chloride tablet prepared from a multiplicity of potassium chloride crystals coated with two distinct layers, the first of ethylcellulose and the second of an least one hydrophilic polymer, preferably hydroxypropylcellulose, resulting in microcapsules. These microcapsules are capable of being compressed into tablets of suitable hardness and friability with minimum quantities of excipients and without disruption of the ethylcellulose rate controlling membrane.

DETAILED DESCRIPTION OF THE INVENTION

A plurality of potassium chloride crystals, preferably from about 20 mesh to about 70 mesh, more preferably from about 30 mesh to about 50 mesh, are coated with two distinct layers. The first layer applied to the crystals is composed of ethylcellulose, preferably with a viscosity of from about 90 to about 110 cp. such as Ethocel 100 (Dow Chemical). Utilization of this high viscosity ethylcellulose allows the crystals to retain their diffusion controlling characteristics even after compression into a tablet form. The ethylcellulose may be applied by any suitable technique known in the art, preferably by coacervation using polyethylene as a phase separator. If coacervation is used, trace amounts of the phase separator may be present in the first layer, preferably in an amount less than about one percent by weight of the ethylcellulose coated crystals. The ethylcellulose layer comprises from about 8 to about 19.5 percent, more preferably from about 11 to about 15 percent, of the total weight of the uncoated potassium chloride crystals. This first layer controls the release of the potassium chloride over time, total release time being proportionally dependent upon the thickness of ethylcellulose. After application of the ethylcellulose, a drying step should preferably be carried out for such a time period and at such temperatures so that the microencapsulated crystals do not adhere to other microcapsules. The resultant ethylcellulose encapsulated potassium chloride microcapsules are preferably of such a size that less than 5% are greater than 20 mesh.

A second, discrete layer of at least one hydrophilic polymer coating, preferable a hydroxypropylcellulose, such as Klucel LF (Aqualon Company), is applied over the first layer of ethylcellulose. Other hydrophilic polymer coatings include, but are not limited to, polyvinyl alcohol, polyvinyl pyrrolidone, and hydroxypropyl methylcellulose. The hydrophilic layer is applied by conventional techniques, such as from an aqueous solution using a fluidized bed coater, to the preformed layer of ethylcellulose. The hydrophilic polymer coating layer comprises from about 0.5 to about 4 percent, more preferably from about 0.5 to about 1.5 percent, of the weight of the ethylcellulose coated crystals. The hydrophilic polymer does not significantly diffuse into the ethylcellulose, but rather forms a distinct second layer. As this layer is soluble to gastric fluids, the hydrophilic polymer coating dissolves following ingestion of the resultant tablet. For all practical purposes, it does not contribute to the controlled release of potassium chloride. Rather, the hydrophilic polymer coating is present primarily as a binder material so that a high dosage rate tablet can be formed with a minimal amount of conventional excipients and low compaction pressures to allow minimal disruption of the rate controlling ethylcellulose membrane.

After the hydrophilic polymer coating layer is applied, the now double coated crystals are subjected to a final drying step The resultant coated potassium chloride microcapsules are preferably of such a size that less than 15% are greater than 20 mesh. The coated crystals may then be formed into tablets by compression using conventional techniques. A minimal amount of excipients, no more than about 15% more preferably no more than 12%, and most preferably no more than 7%, by weight of the final dosage tablet, is added to the coated crystals prior to compression. This is in contrast to the greater than 30% excipients typically necessary for compression of potassium chloride microcapsules without a hydrophilic coating layer into a tablet form. In addition, this formulation allows the microencapsulated potassium chloride to be dispersed essentially intact over a wide area, reducing the risk of gastric irritation.

The term "excipients", as used herein, refers to any additional pharmaceutically acceptable ingredients which may be used in a tablet. These excipients include, but are not limited to, ingredients such as binders, disintegrants, wetting agents, and lubricating agents. Binders include, but are not limited to, Klucel® LF (hydroxypropylcellulose) and Avicel® (microcrystalline cellulose). Disintegrants include, but are not limited to, cornstrach, lactose, mannitol, sucrose, Avicel® (microcrystalline cellulose), Primogel® (sodium carboxymethyl starch, Emcompress® (dibasic calcium phosphate dihydrate), Crospovidone® (cross linked polyvinyl pyrrolidone), and tricalcium phospate. Wetting agents include, but are not limited to, sodium lauryl sulfate. Lubricating agents include, but are not limited to stearates (e.g. magnesium, calcium, and sodium,) stearic acid, Sterotex®, talc, waxes, and Stearowet®.

The final tablets will contain a pharmaceutically acceptable amount of potassium chloride to treat humans in need thereof, preferably from about 8 mEq to about 20 mEq. Acceptable daily dosages may be found in *The Physicians' Desk Reference*, 45th ed. (1991), e.g. 20–200 mEq/day.

EXAMPLES

Example 1

The coated potassium chloride microcapsules of the present invention may be produced by coacervation as follows:

| Ingredient | Amount |
|---|---|
| Potassium Chloride, USP | 567 kg |
| Cyclohexane | 875 gal |
| Ethylcellulose, NF | 83.5 kg |
| Polyethylene | 58 kg |
| Hydroxypropyl Cellulose, NF | 6.9 kg |
| Purified Water, USP | 35 kg |

The potassium chloride, cyclohexane, ethylcellulose, and polyethylene are mixed together with controlled agitation and heating until the polymers are in solution. The solution is then cooled to achieve encapsulation of the potassium chloride with the ethylcellulose. The resulting microcapsule slurry is next filtered using a rotary vacuum filter and the resulting wet microcapsules are dried in a fluidized bed drier. The dry microcapsules are sized, preferably through a 14 mesh sieve to produce potassium chloride microcapsules ready for coating.

A solution of hydroxypropylcellulose and purified water is prepared. The potassium chloride microcapsules are coated with this solution using a fluidized bed coater. The resulting coated microcapsules are then dried and sized through a 12 mesh sieve.

By the foregoing technique, other hydrophilic polymers which provide a binding effect may be used, i.e. polyvinyl alcohol, polyvinyl pyrrolidone, and hydroxypropyl methylcellullose, which have found acceptance in coating pharmaceuticals.

Example 2

The release rate of the microcapsules of Example 1 were measured using the USP Basket Method, 900 ml purified water, 100 rpm at 37 degrees C.

| | Release Rate (%/hour) | | |
|---|---|---|---|
| Time (hours) | Trial 1 | Trial 2 | Trial 3 |
| 1 | 21.8 | 17.6 | 15.0 |
| 4 | 71.3 | 57.6 | 54.7 |
| 8 | 99.5 | 92.1 | 89.6 |

Example 3

The microcapsules of Example 1 are used to prepare 20 mEq potassium chloride tablets using conventional tabletting techniques, e.g. compressed on an instrumented rotary tablet press, and conventional tabletting excipients, e.g. binders, disintegrants, wetting agents, and lubricating agents. The release rate of the potassium chloride tablets were measured using the USP Basket Method, 900 ml purified water, 100 rpm at 37 degrees C.

| | Release Rate (%/hour) | | |
|---|---|---|---|
| Time (hours) | Trial 1 | Trial 2 | Trial 3 |
| 1 | 21.4 | 22.0 | 17.0 |
| 2 | 40.0 | 36.9 | 33.2 |
| 4 | 71.6 | 65.1 | 60.8 |
| 6 | 90.2 | 87.3 | 84.5 |
| 8 | 99.4 | 101.3 | 97.4 |

Example 4

The coated potassium chloride microcapsules of Example 1 were made into tablets using conventional tabletting techniques and the following formulation:

| Ingredient | Percent |
|---|---|
| Coated KCL microcapsules | 88 |
| Microcystalline cellulose | 10 |
| Cross-linked polyvinyl pyrrolidone | 2 |

The potassium chloride microcapsules of Example 1 were also prepared without the hydroxypropylcellulose coating or any other hydrophilic polymer coating. These uncoated microcapsules could not be made into tablets using conventional tabletting techniques and the above formulation. The amount of KCl microcapsules in the formulation had to be decreased to about 68% in order that they might be tabletted using conventional tabletting techniques.

The above description is for the purpose of teaching the person of ordinary skill in the art how to practice the present invention and is not intended to detail all those obvious modifications and variations of it which will become apparent to the skilled worker upon reading the description or to limit the invention in any way. It is intended, however, that all such obvious modifications and variations be included within the scope of the present invention and by the following claims.

What is claimed is:

1. A microcapsule comprising:
   (a) a crystal of potassium chloride;
   (b) a first layer on said crystal consisting essentially of ethylcellulose; and
   (c) a second distinct layer over said first layer comprising at least one hydrophilic polymer.

2. The microcapsule of claim 1, wherein the potassium chloride crystal is between about 20 and about 70 mesh.

3. The microcapsule of claim 1, wherein the hydrophilic polymer is hydroxypropylcellulose.

4. The microcapsule of claim 1, wherein the hydrophilic polymer is polyvinyl alcohol.

5. A sustained release tablet comprising a plurality of the microcapsules of claim 1 and at least one excipient in an amount of no more than about 15%.

6. A sustained release tablet comprising a plurality of the microcapsules of claim 1 and at least one excipient in an amount of no more than about 12%.

7. A sustained release tablet comprising a plurality of the microcapsules of claim 1 and at least one excipient in an amount of no more than about 7%.

8. The tablet of claim 1, wherein the potassium chloride is in an amount effective to treat potassium deficiency of a human.

9. The tablet of claim 1, wherein the amount of potassium chloride is frown about 8 to about 20 mEq.

10. A method of treating potassium deficiency in humans by oral administration of the tablet of claim 1.

* * * * *